US006355626B1

(12) United States Patent
Panettieri et al.

(10) Patent No.: US 6,355,626 B1
(45) Date of Patent: Mar. 12, 2002

(54) ANTITHROMBIN AGENTS IN TREATMENT OF ASTHMA

(75) Inventors: Reynold Panettieri, Ambler; Richard Murray, Philadelphia, both of PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 08/242,728

(22) Filed: May 13, 1994

(51) Int. Cl.[7] .................. A01N 43/04; A61K 31/715
(52) U.S. Cl. ............................. 514/56; 514/54
(58) Field of Search ........................ 514/54, 56

(56) References Cited

U.S. PATENT DOCUMENTS 5,380,716 A * 1/1995 Conrad et al. ............ 514/56

OTHER PUBLICATIONS

Grynkiewicz, G, et al., "A New Generation of $Ca^{2+}$ Indicators with Greatly Improved Fluorescence Properties", *J. Biol. Chem.*, 260:3440–3450, 1985.

Hung, David T., et al., "Mirror Image Antagonists of Thrombin–induced Platelet Activation Based on Thrombin Receptor Structure", *J. Clin. Invest.*, 89:444, 1992.

Kameyoshi, Y., et al., "Cytokine RANTES Released by Thrombin–stimulated Platelets Is a Potent Attractant for Human Eosinophils", *J. Exp. Med.*, 176:587, 1992.

Kobayashi, S., et al., "Effects of an Antithrombotic Agent (MD–805) on Progressing Cerebral Thrombosis", *Throm. Res.*, 53:305–317, 1989.

Murray, R.K., et al., "Receptor–Activated Calcium Influx in Human Airway Smooth Muscle Cells", *J. Physiol. Lond.*, 435:123–144, 1991.

Murray, R.K., et al., "Receptor–activated Ca Influx in Human Airway Smooth Muscle: Use of Ca Imaging and Perforated Patch–clamp Techniques", *Am. J. Physiol.*, 264 (Cell Physiol.33):C485–490, 1993.

Roth, M., et al., "Inhibition of Receptor–mediated Platelet Activation by Nedocromil Sodium", *J. Allergy Clin. Immunol.*, 91(6):1217, 1993.

Vinazzer, H., "Therapeutic Use of Antithrombin III in Shock and Disseminated Intravascular Coagulation", *Throm. Hemo.*, 15:347–352, 1989.

* cited by examiner

Primary Examiner—Theodore J. Criares
(74) Attorney, Agent, or Firm—Licata & Tyrrell P.C.

(57) ABSTRACT

Methods of inhibiting calcium release and proliferation in human airway smooth muscle cells by contacting cells with an antithrombin agent are provided. These antithrombin agents are useful in the treatment of asthma.

1 Claim, 4 Drawing Sheets

ANTITHROMBIN AGENTS IN TREATMENT OF ASTHMA

BACKGROUND OF THE INVENTION

Thrombin is an important activator of both fibrin clot formation and platelet plug formation and plays a central role in hemostasis, thrombosis, and atherosclerosis. Thrombin is an active form of an enzyme normally present in plasma as an inactive precursor, prothrombin. When vascular damage exposes tissue factor to the circulation, prothrombin is converted to thrombin, thus making the enzyme available to activate platelets.

Thrombosis in arterial circulations is a leading cause of death today. Platelet activation by thrombin is believed to be a critical event in the development of arterial thrombosis. Based on structure-activity studies of a cloned platelet thrombin receptor, two antagonists of thrombin and thrombin receptor function were designed. Hung et al., *J. Clin. Invest.* 89:444, 1992. The first antagonist, an "uncleavable" peptide mimicking the receptor domain postulated to interact with thrombin, was shown to be potent thrombin inhibitor. The second, a proteolytically inactive mutant thrombin designed to bind but not cleave the thrombin receptor, was also found to be a specific antagonist of receptor activation by thrombin.

Stimulation of platelets has also been shown to result in the release of various mediators that may lead to an extension of inflammation and intensify the immune response. Recent reports have suggested that platelets may play an important role in the inflammatory process of human asthma. Therefore several researchers have been studying the effects of thrombin on platelet aggregation and its effects on asthma.

Nedocromil sodium is used therapeutically as an antiinflammatory drug in the treatment of asthma. Roth et al., *J. Allergy Clin Immunol.*, 91(6):1217, 1993, demonstrated that nedocromil sodium interferes with thrombin- and platelet activating factor-mediated platelet activation. The inhibition of platelet activation demonstrated in these studies was proposed to contribute to the antiinflammatory effects of nedocromil sodium in asthma.

Thrombin stimulation of human platelets has also been shown to result in the release of a preformed proteinaceous human eosinophil (Eo) chemotactic activity. Kameoyoshi et al., *J. Exp Med.* 176:587, 1992. This finding was suggested to serve as additional evidence for the recent understanding that platelets contribute to inflammatory reactions of allergic asthma.

It has now been found that thrombin potently and effectively increases cytosolic calcium release in human airway smooth muscle, which is required for smooth muscle contraction and stimulates human airway smooth muscle cell proliferation. Inhibition of the activities of thrombin upon human airway smooth muscle through use of thrombin receptor antagonists and/or antithrombin agents is useful as a treatment of bronchospasm and asthma.

SUMMARY OF THE INVENTION

An object of the present invention is to provide a method of inhibiting cytosolic calcium release in human airway smooth muscle cells that comprises treating human airway smooth muscle cells with an effective amount of an antithrombin agent so that release of cytosolic calcium is inhibited. The use of antithrombin agents to inhibit cytosolic calcium release in these cells is also provided.

Another object of the present invention is to provide a method of inhibiting proliferation of human airway smooth muscle cells comprising treating human airway smooth muscle cells with an effective amount of an antithrombin agent so that proliferation of human airway smooth muscle cells is inhibited. The use of antithrombin agents to inhibit proliferation of these cells is also provided.

Yet another object of the present invention is to provide a method of treating asthma in an individual suffering from asthma comprising administering to said individual an effective amount of an antithrombin agent so that smooth muscle contraction and proliferation of smooth airway smooth muscle cells which occurs in individuals suffering from asthma is inhibited. The use of antithrombin agents to treat asthma is also provided.

DETAILED DESCRIPTION OF THE INVENTION

Figure 1:
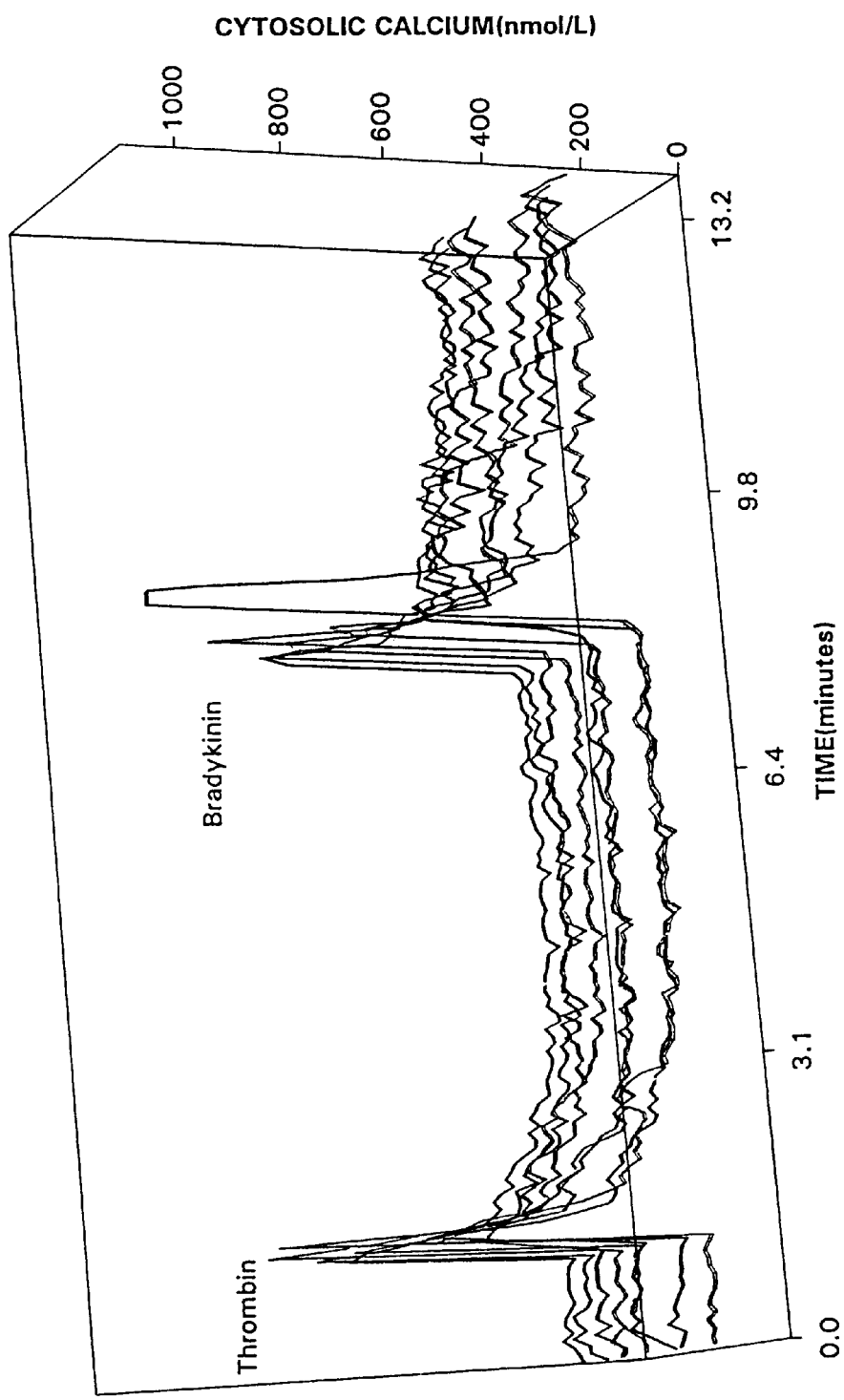
FIG. 1 is a graph showing the time course of cytosolic calcium (nmol/l) in eight individual cells. In response to α-thrombin (0.3 U/ml) all cells demonstrated a rapid rise in calcium which then returned to baseline. A subsequent addition of bradykinin (1 μM) evoked a similar response.

Asthma, a chronic disease characterized by airway hyperactivity and bronchoconstriction, occurs in 5–8% of the U.S. population and is an extraordinarily common cause of pulmonary impairment. Despite considerable research efforts, the precise cellular and molecular mechanisms that induce airway hyperactivity in asthmatics remains unknown. Studies have shown, however, that airway inflammation is important in stimulating airway smooth muscle contraction that results in bronchoconstriction. Mononuclear cells recruited into the airway are stimulated to release inflammatory mediators. Release of these newly formed mediators as well as eicosonoids induce edema of the bronchial submucosa by increasing vascular permeability. This increase in vascular permeability results in the capillary leakage of serum proteins which activate thrombin. It has now been determined that thrombin potently induces cytosolic calcium release required for human airway smooth muscle (ASM) cell contraction and stimulates human ASM cell proliferation.

Thrombin is a key enzyme in the coagulation cascade, being the final effector responsible for the conversion of fibrinogen to fibrin. Research efforts have primarily focused upon the effects of thrombin in promoting cardiovascular diseases. Antithrombin agents and thrombin receptor antagonists have been proposed as possible therapeutics in the treatment of atherosclerosis. It has now been found that these agents are useful in the treatment of asthma.

In the present invention it is taught that thrombin is capable of inducing calcium mobilization, polyphosphoinositide hydrolysis and cell proliferation in human ASM cells. In a dose and time-dependent manner, thrombin was found to induce increases in cytosolic calcium and polyphosphoinositide hydrolysis. Addition of α-thrombin to fura-2-loaded humah ASM cells produced a prompt rise in cytosolic calcium followed by a return towards baseline in a pattern similar to that produced by known contractile agonists such as bradykinin. In fact, in studies designed to compare the magnitude of α-thrombin-evoked increases in cytosolic calcium with those evoked by bradykinin, no significant differences were observed between the two.

In the present invention a method of inhibiting cytosolic calcium release in human airway smooth muscle cells is provided which comprises contacting human airway smooth muscle cells with an effective amount of an antithrombin agent so that cytosolic calcium release is inhibited. When an antithrombin agent, such as the thrombin antagonist r-hirudin, was added to fura-2-loaded human ASM cells, subsequent addition of α-thrombin failed to evoke a rise in cytosolic calcium levels. Thus, antithrombin agents can be used to inhibit the release of cytosolic calcium in human ASM cells.

Cytosolic calcium release is associated with the contraction process in smooth muscle cells. In a relaxed muscle ATP is bound to the head of a myosin molecule. Though energy is available for contraction, no contraction occurs because the troponin-tropomyosin complex on the thin filaments blocks the myosin binding sites on the actin. When calcium ions are released into the cytoplasm of the cell, however, the calcium ions bind to troponin causing a change in its molecular configuration. This in turn alters the structure of the troponin-tropomyosin complex resulting in a shift in the position of this complex on the surface of the actin filaments. This shift exposes previously covered active sites on the surface of the actin molecule wherein myosin can bind or cross bridge. This cross bridging results in a sliding of the actin filaments which shortens the smooth muscle cell and causes contraction. Inhibition in the release of calcium ions results in a decrease in smooth muscle cell contraction. Thus, contacting human ASM cells with an effective amount of an antithrombin agent results in a decrease in human ASM cell contraction.

In the present invention a method is also provided for the inhibition of proliferation of human airway smooth muscle cells. Increased airway smooth muscle mass, which is due to increases in ASM cell proliferation, is a commonly reported pathologic finding in patient's with sever asthma. Contacting human airway smooth muscle cells with an effective amount of an antithrombin agent has now been found to inhibit proliferation of these cells. α-Thrombin has been found to stimulate DNA synthesis in a concentration dependent manner, inducing a 20–22 fold increase in [$^3$H]-thymidine incorporation over controls. This increase was found to correlate with an increase in cell number, thus indicating that α-thrombin is mitogenic for human ASM cells. The mitogenic effects of α-thrombin on human ASM cells are inhibited by antithrombin agents. Pretreating cells with the thrombin antagonist, r-hirudin, inhibited the proliferation in these cells resulting from α-thrombin stimulation in a concentration-dependent manner. The selectivity of r-hirudin was determined by measuring DNA synthesis in cells stimulated with EGF. r-Hirudin pretreatment had no significant effect on EGF-induced DNA synthesis in human ASM cells. Thus, antithrombin agents can be used to inhibit the proliferation of humans ASM cells associated with α-thrombin. This proliferation has been associated with the hyperplasia of airway smooth muscle in severe asthmatics.

Asthma is a disease characterized by airway inflammation, hyperresponsiveness, bronchial smooth muscle contraction and, in severe asthmatics, airway smooth muscle hyperplasia. In the present invention a method is provided for the treatment of asthma and related symptoms in an individual suffering from asthma which comprises administering to said individual an effective amount of an antithrombin agent. Administration of an antithrombin agents has been shown to inhibit the release of cytosolic calcium leading to human ASM cell contraction and proliferation of human ASM cells. Such agents can be used to inhibit the bronchospasm and airway smooth muscle hyperplasia associated with asthma.

Several antithrombin agents have been developed recently and studies in humans have reported doses at which these compounds inhibit plasma thrombin activity without untoward side effects.

Antithrombin-III (Immuno AG, Austria) has been studied in the treatment of disseminated intravascular coagulation. Vinazzer, H., *Semin. Throm. Hemo.*, 15:347–352, 1989. The effects of a synthetic selective antithrombin agent, MD-805, on progressive cerebral thrombosis has also been studied. Kobayashi, S. et al., *Throm. Res.*, 53:305–317, 1989. These studies have determined that antithrombin agents are safe and effective in the treatment of patients with disseminated intravascular coagulation as well as cerebral thrombosis.

Antithrombin agents such as antithrombin-III and MD-805 can also be used in the treatment of asthma. Such compounds can be administered intravenously, subcutaneously or via inhalation. Since asthma is a lung disease characterized by airway obstruction, drug delivery may be optimized by direct administration to the lungs via inhalation therapy. This mode of drug administration will greatly decrease the likelihood of any systemic side effects while improving drug delivery to the lungs. Persons of ordinary skill can easily determine optimum dosages, dosing methodologies and repetition rates in accordance with the weight and condition of the patient.

For the purposes of this invention the term "effective amount" refers to a concentration of an antithrombin agent which inhibits the α-thrombin-induced effect upon human ASM cells. By "inhibit", "inhibiting" and "inhibition" it is meant that there is a decrease from the normal level of response the human ASM cell has to α-thrombin. By "antithrombin agent" is meant to include any compound which deters the normal activities evoked by the presence of thrombin. Examples include, but are not limited to, thrombin antagonists such as r-hirudin and the antithrombin agents antithrombin III and MD-PENN-805.

The invention is further illustrated by the following non-limiting examples.

EXAMPLES

Example 1

Airway Smooth Muscle (ASM) Cell Culture

Human trachea was obtained from lung transplant donors. A segment of trachea just proximal to the carina was removed under sterile conditions and the trachealis muscle was isolated. Approximately 0.5 grams of wet tissue is obtained through this technique. The tissue was minced, centrifuged at 1,000 g for 10 minutes, and resuspended in buffer (10 ml) containing 0.2 mM $CaCl_2$, 640 U/ml collagenase, 1 mg/ml soybean trypsin inhibitor and 10 U/ml elastase. Enzymatic dissociation of the tissue was performed for 90 minutes in a shaking water bath at 37° C. The cell suspension was filtered through 105 µm nylon mesh, and the filtrate was washed with equal volumes of cold Ham's F12 medium supplemented with 10% fetal bovine serum (FBS). Aliquots of the cell suspension were plated at a density of $1.0 \times 10^4$ cells/$cm^2$. Ham's F12 medium was supplemented with 10% FBS, 1.000 U/ml penicillin, 1 mg/ml streptomycin, and 2.5 µg/ml amphotericin B and was replaced every 72 hours. Cell counts were obtained in triplicate wells with 0.5% trypsin in 1 mM EDTA solution.

Human ASM cells in subculture during the 2nd and 5th cell passage were used in all experiments because, during these cell passages, the cells retain native contractile protein expression as demonstrated by immunocytochemical staining for smooth muscle actin and myosin. Further these cells retain functional cell-excitation coupling systems as determined by fura-2 measurements of agonist-induced changes in cytosolic calcium.

Example 2

Cytosolic Calcium Measurements

Measurements of thrombin-induced changes in cytosolic calcium were performed on bradykinin sensitive lines of human airway smooth muscle cells. Cultured human ASM cells were grown on 22-mm glass cover slips and loaded with fura-2/AM (2.5 µM in medium M199), supplemented with 1 mg/ml of bovine serum albumin, for 30 minutes at 37° C.). After loading with fura-2, cells were washed with a HEPES-buffered saline solution, as described by Murray R K, et al., *J. Physiol. Lond.*, 435:123–144, 1991, and placed in a thermostatically controlled cell chamber on an inverted microscope. Cells were imaged using a 40× (oil) fluorescence objective lens. Excitation energy was switched between a 340 nm and 380 nm wavelength emitted from a 75 watt xenon lamp source via a fura-2 dichroic mirror (Chroma Technology, Battleboro, Vt.). After passing through the dichroic meter, the emission fluorescence passed through a 510 nm wavelength filter and was diverted to an image-intensified CCD camera attached to a video side port of the microscope. Images were digitized using a video A to D board. Image analysis of individual cursor-defined regions corresponding to individual cells was accomplished using the Image-1 AT/fluor program (Universal Imaging, West Chester, Pa.). The 340:380 nm wavelength ratio was converted to an estimate of cytosolic calcium using the calibration method described by Murry R K, et al., *Am. J. Physiol.*, 264 (Cell Physiol.33):C485–490, 1993, and Grynkiewicz G, et al., *J. Biol. Chem.*, 260:3440–3450, 1985.

Calibration measurements were made using ionomycin (10 µM) and added calcium (total calcium=12 mM) to measure $R_{max}$ or addition of a stoichiometric excess of EGTA to achieve $R_{min}$. Values used for the calibration equation were $R_{min}$=0.3, $R_{max}$=5.0, Kd=224 nM and $f380_{min}/f380_{max}$=5. In most experiments, the extracellular calcium was maintained at 2 mM, although in some experiments designed to separate intracellular release from calcium influx, cells were activated using nominally calcium-free extracellular buffer (HEPES-buffered saline solution with no added calcium). Additions of plasminogen-free bovine α-thrombin (0.01 unit/ml through 1 unit/ml) were made by direct bath additions. In some experiments, r-hirudin (10,000 ATU/mg protein) was added prior to addition of thrombin. r-Hirudin is a leech-derived recombinant protein that functions as a thrombin antagonist. In some experiments, bradykinin (1 µM) was added to compare the magnitude of bradykinin-induced calcium transients with those evoked by a maximum dose of thrombin.

Figure 2:
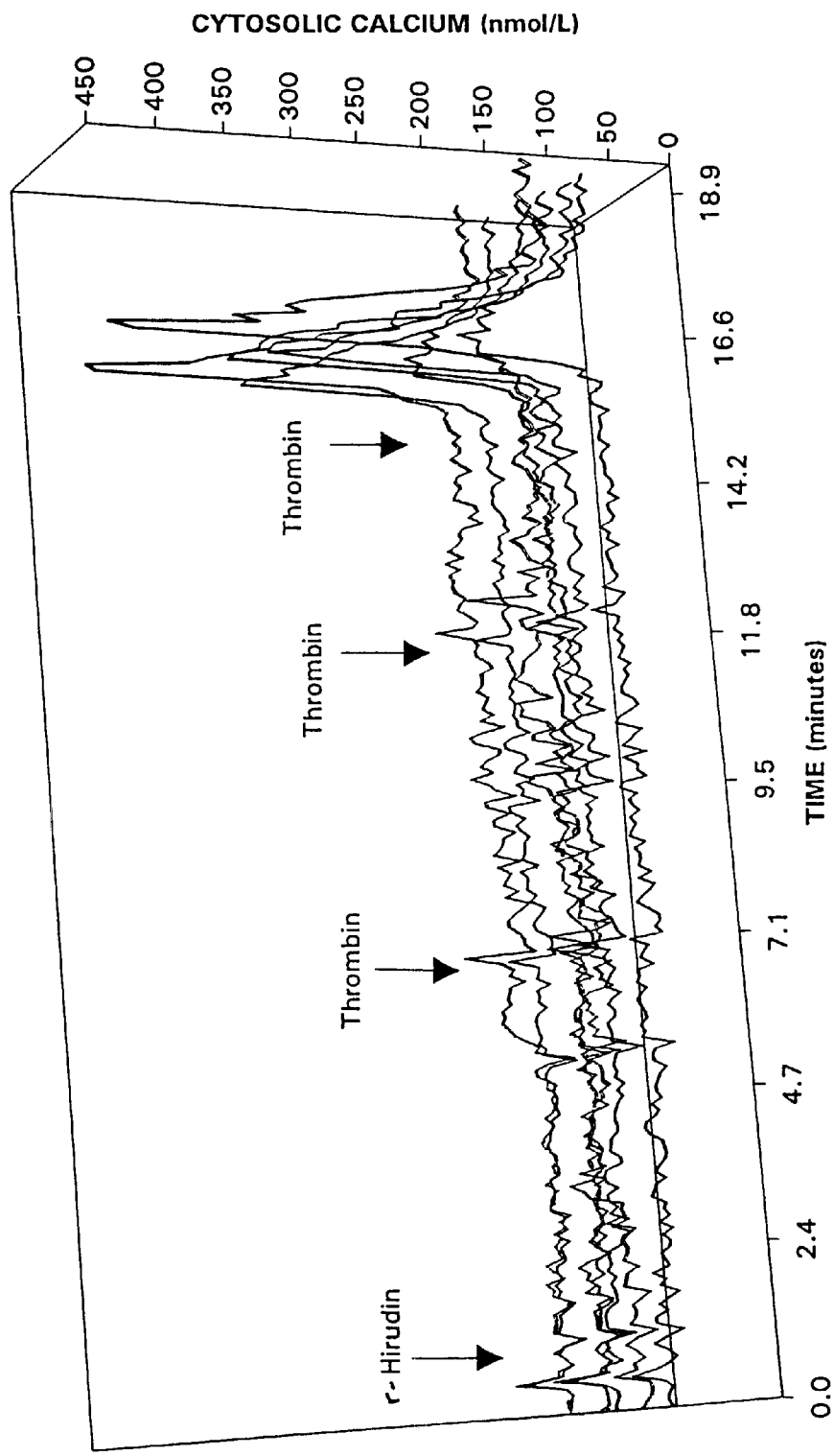
FIG. 2 is a graph showing the time course of cytosolic calcium in seven individual cells. Addition of r-hirudin did not cause a change in calcium levels. α-Thrombin (0.3 U/ml) failed to evoke a response in cells pretreated with r-hirudin despite two additions. Only after addition of 1 U/ml α-thrombin was a calcium response evoked in these cells.

The addition of α-thrombin (0.3 units/ml) to fura-2-loaded ASM cells is followed by a large increase in calcium. (See FIG. 1). When r-hirudin (5 units/ml), a thrombin antagonist, was added to fura-2-loaded human ASM cells, there as no change in baseline cytosolic calcium. (See FIG. 2). Subsequent additions of 0.3 units of α-thrombin in two separate aliquots failed to evoke the release of calcium in these cells. A third addition of α-thrombin (1 unit/ml) was able to overcome the r-hirudin block and evoke that calcium release in most of the cells.

Example 3

[$^3$H]-Thymidine and Cell Proliferation Assays

Figure 3:
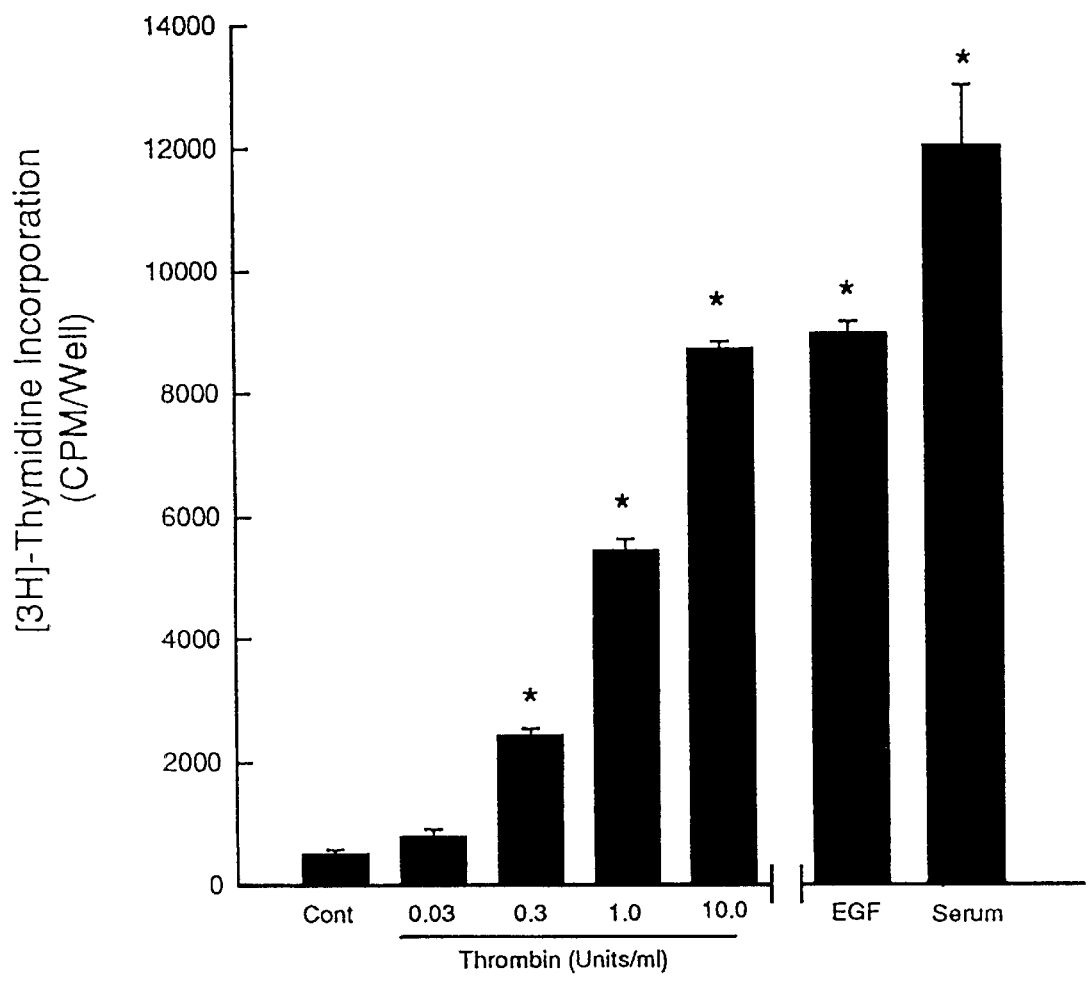
FIG. 3 is a bar graph showing [$^3$H]-thymidine incorporation in confluent, growth-arrested ASM cells that were stimulated with either 0.03, 0.3, 1.0, or 10 NIH Units/ml α-thrombin as compared with cells treated with vehicle alone, 10% serum of 100 ng/ml epidermal growth factor (EGF).
Figure 4:
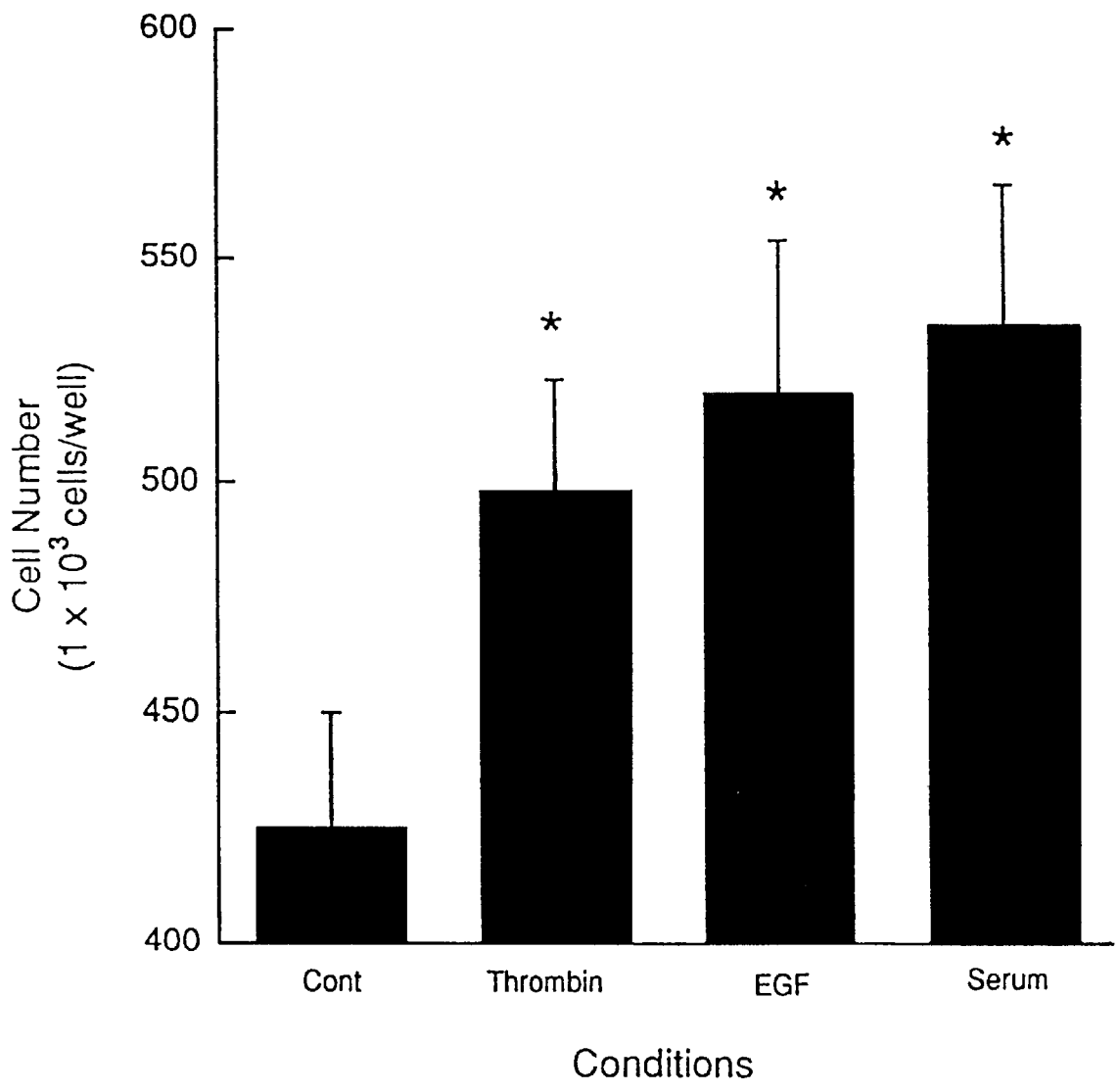
FIG. 4 is a bar graph showing the number of cells counted in confluent, growth-arrested ASM cells that were stimulated with α-thrombin (1.0 unit/ml), 100 ng/ml EGF, 10% serum, or vehicle alone for 36 hours. Data represent means±SEM from four separate experiments each containing four replicates for each stimulation group. Statistical significance was determined using a one way ANOVA test (Bonferroni-Dunn) [experimental condition v. control; * $P<0.01$].

Proliferation studies were performed on confluent, growth-arrested human ASM cells. Cells were growth arrested by incubating the cultures at day 10 in serum-free media consisting of F12 media with 5 ng/ml insulin, and 5 ng.ml transferrin. Confluent, growth-arrested cells were used because cells can be synchronized in the $G_0/G_1$ phase of the cell cycle and, at this baseline, minimally incorporate [$^{35}$S]-methionine and [$^3$H]-thymidine. After 24 hours in serum-free media, the cells were then stimulated with either 100 ng/ml EGF (purchased from Sigma Chemical Co., St. Louis, Mo.), 10% FBS, or varying doses of plasminogen-free bovine α-thrombin [100 NIH units/mg protein] (purchased from Calbiochem, La Jolla, Calif.). In separate experiments, the cells were pretreated with r-hirudin and stimulated in a similar manner as described above. After 16–18 hours of mitogen stimulation, human ASM cells were labeled with 1.0 µCi/ml of [methyl-$^3$H]-thymidine [40–60 Ci/mmol] (purchased from Amersham Corp., Arlington Hts., Ill.) for 12–18 hours. The cells were then scraped, lysed and the protein/DNA precipitated with 12% trichloroacetic acid. The precipitant was aspirated onto glass filters, extensively washed with phosphate buffered saline, dried and counted. [$^3$H]-thymidine incorporation experiments were confirmed by cell proliferation assays and compared with control cells that were maintained in serum-free conditions alone or were stimulated with either EGF, α-thrombin or serum. After removing cells from the wells with 0.5% trypsin-1 mM EDTA solution, cell counts were obtained from each well using a Coulter Counter (Coulter Electronics, Hialeah, Fla.). The proliferation assays were performed with a minimum of three different cell lines.

α-Thrombin stimulated DNA synthesis in a concentration dependent manner, inducing a 20–22 fold increase in [3H] thymidine incorporation as compared with cells treated with vehicle alone (See FIG. 3). α-Thrombin maximally stimulated DNA synthesis at concentration of 10 units/ml; the EC50 was approximately 1.0 unit/ml. These increase in DNA synthesis were detectable after 18 hours of stimulation, however, maximal effects occurred between 36 and 38 hours. After 36 hours of stimulation, α-thrombin stimulated a 17.6%±2.0% increase in cell number as compared with cells treated with vehicle alone (See FIG. 4).

To address the selectivity of α-thrombin effects on DNA synthesis, it was determined the r-hirudin inhibited α-thrombin-induced increases in thymidine incorporation. In a concentration dependent manner, DNA synthesis in cell pretreated with 0.2 units/ml or 2.0 units/ml r-hirudin was inhibited 27.2%±1.8% and 98.8%±1.2% respectively as compared with cells treated with α-thrombin alone. r-Hirudin pretreatment had no significant effect on EGF-induced DNA synthesis in human ASM cells.

Example 4

Clinical Studies

The effects of antithrombin-III and MD-805 in the treatment of asthmatics with doses that range for 1U-1000U daily of antithrombin-III or from 10 mg to 60 mg daily of MD-305 are determined in a double blinded, crossover-controlled manner in a 24-week study. Sixty (60) patients with asthma (as defined by the American Thoracic Society) are enrolled in the study if they were non-smokers, were at least 18 years old, and had required daily drug treatment of their asthma for at least six months before the start of the study. At screening the subjects had to have a forced expiratory volume of one second ($FEV_1$) of 50 to 80 percent predicted values after asthma medications had been withheld. Bronchospasm is defined as reversible if the $FEV_1$ increased by at least 15% above base line within 30 min after two inhalations of albuterol, a common bronchodilator.

All subjects enrolled in the study complete a preprandomization (base line) assessment period from 7 to 14 days, during which the dosages of inhaled corticosteroids or cromyln is held constant; the use of β-agonists is limited to inhaled albuterol as needed; short-acting and sustained-release theophylline is withheld for 24 and 48 hours, respectively, before pulmonary-function testing at screening and on the first day of treatment. Inhaled albuterol is also withheld for at least 8 hours.

Patients are assigned to treatment with either antithrombin-III (1U-1000U twice daily) or MD-805 (10–60 mg twice daily), or placebo, according to a randomized schedule. At the completion of a 12 week trial, the patients will have a 2 week washout interval and receive no experimental medications to establish baseline studies. Subsequently, subjects will be randomly assigned to one of the other treatment groups. All patients can use albuterol supplementally for short-term relief of asthma symptoms. Patients receiving inhaled corticosteroids or cromyln are eligible for enrollment, but the dosages of these medications is to be held constant throughout the study. The use of theophylline or oral β-agonists during the treatment phase is not allowed.

Outcome Measures. Each patient receives a peak flow meter at the first visit, with instructions to record on diary cards the best of three successive determinations the peak expiratory flow rate (PEF) every morning before the first dose of study drug and every evening before the last dose of study drug. The patient is also asked to record the presence and severity of symptoms (wheezing, shortness of breath, coughing and chest tightness), the number of times per night that he or she awakens by symptoms of asthma, and the number of puffs of supplemental albuterol used each day.

On the first day of treatment and after 4, 8, and 12 weeks of treatment, the $FEV_1$, forced vital capacity (FVC), and forced midexpiratory flow rate ($FEF_{25-75}$) is measured 30 minutes before and immediately before the first dose and then hourly for 12 hours. Also at these study visits, electrocardiography is performed as well as prothrombin times, partial thromboplastin times and bleeding times.

Efficacy analyses is based on the following variables: the FEV1, FVC, and $FEF_{25-75}$: the number of patients whose FEV, will increase >15%, the number of episodes of exacerbations of asthma (defined as a worsening of asthma that was not controlled by supplemental albuterol and that required additional therapy); and data from diary (i.e. PEF, symptoms, and frequency of supplemental use of albuterol). Safety analyses is based on the number of clinical adverse events, vital signs, and changes in laboratory and electrocardiographic values.

What is claimed is:

1. A method of inhibiting proliferation of human airway smooth muscle cells comprising contacting human airway smooth muscle cells with an effective amount of an antithrombin agent so that proliferation of said cells is inhibited.

* * * * *